(12) United States Patent
Baek et al.

(10) Patent No.: US 9,706,978 B2
(45) Date of Patent: Jul. 18, 2017

(54) ULTRASOUND SYSTEM AND METHOD FOR PROVIDING GUIDE LINE OF NEEDLE

(71) Applicant: SAMSUNG MEDISON CO., LTD., Gangwon-do (KR)

(72) Inventors: Ji-hye Baek, Gangwon-do (KR); Jong-sik Kim, Gangwon-do (KR)

(73) Assignee: SAMSUNG MEDISON CO., LTD., Hongcheon-gun, Gangwon-do (KR)

( * ) Notice: Subject to any disclaimer, the term of this patent is extended or adjusted under 35 U.S.C. 154(b) by 556 days.

(21) Appl. No.: 14/073,331

(22) Filed: Nov. 6, 2013

(65) Prior Publication Data
US 2014/0128728 A1 May 8, 2014

(30) Foreign Application Priority Data

Nov. 7, 2012 (KR) .................. 10-2012-0125597

(51) Int. Cl.
*A61B 8/08* (2006.01)
*G06T 7/11* (2017.01)
(Continued)

(52) U.S. Cl.
CPC .......... *A61B 8/5207* (2013.01); *A61B 8/0841* (2013.01); *A61B 8/5246* (2013.01);
(Continued)

(58) Field of Classification Search
CPC ... A61B 8/5207; A61B 8/5246; A61B 8/0841; A61B 8/5223; A61B 8/14; A61B 8/1477;
(Continued)

(56) References Cited

U.S. PATENT DOCUMENTS 6,216,029 B1 4/2001 Paltieli
6,524,247 B2 2/2003 Zhao et al.
(Continued)

FOREIGN PATENT DOCUMENTS

JP 2000316863 A 11/2000
KR 10-1999-0029038 A 4/1999
KR 10-2006-0119813 A 11/2006

OTHER PUBLICATIONS

European Search Report issued in European Application No. 13191520.9 dated Jan. 8, 2014.
(Continued)

*Primary Examiner* — Long V Le
*Assistant Examiner* — Angela M Hoffa
(74) *Attorney, Agent, or Firm* — McDermott Will & Emery LLP

(57) ABSTRACT

Provided are an ultrasound system and method for providing a guide line corresponding to a pathway through which a needle is introduced or inserted. The ultrasound system includes an ultrasound data acquisition unit that transmits an ultrasound signal to a living body into which the needle is inserted, receives an ultrasound echo signal reflected from the living body, and acquires ultrasound data corresponding to each of a plurality of ultrasound images, and a processor that generates the plurality of ultrasound images by using the ultrasound data, creates a mask image for detecting a position and an angle at which the needle is introduced, detects the position and angle by using the mask image, and sets a guide line of the needle on the ultrasound image by using the position and angle.

16 Claims, 8 Drawing Sheets

(51) Int. Cl.
*A61B 10/02* (2006.01)
*G06T 7/73* (2017.01)
*A61B 18/14* (2006.01)
*A61B 8/14* (2006.01)
*A61B 17/34* (2006.01)
*A61B 90/00* (2016.01)

(52) U.S. Cl.
CPC ............ *A61B 10/0233* (2013.01); *G06T 7/11* (2017.01); *G06T 7/74* (2017.01); *A61B 8/14* (2013.01); *A61B 8/5223* (2013.01); *A61B 18/1477* (2013.01); *A61B 2017/3413* (2013.01); *A61B 2090/378* (2016.02); *G06T 2207/10132* (2013.01); *G06T 2207/30021* (2013.01)

(58) Field of Classification Search
CPC ...... A61B 2017/3413; A61B 2090/378; A61B 10/0233; A61B 18/1477; G06T 7/0044; G06T 7/0081; G06T 2207/10132; G06T 2207/30021; G06T 7/11; G06T 7/74
See application file for complete search history.

(56) References Cited

U.S. PATENT DOCUMENTS

| | | | | |
|---|---|---|---|---|
| 6,733,458 | B1* | 5/2004 | Steins | A61B 8/0833 600/461 |
| 9,226,729 | B2* | 1/2016 | Tashiro | A61B 8/0841 |
| 2007/0016035 | A1 | 1/2007 | Hashimoto | |
| 2009/0093717 | A1 | 4/2009 | Carneiro et al. | |
| 2011/0201931 | A1 | 8/2011 | Palmeri et al. | |
| 2011/0249878 | A1 | 10/2011 | Pagoulatos et al. | |
| 2011/0282188 | A1* | 11/2011 | Burnside | A61B 5/042 600/424 |
| 2012/0078103 | A1* | 3/2012 | Tashiro | A61B 8/0841 600/443 |
| 2012/0253181 | A1 | 10/2012 | Okamura et al. | |
| 2014/0128728 | A1* | 5/2014 | Baek | A61B 8/5207 600/424 |
| 2014/0148689 | A1* | 5/2014 | Lee | G06T 7/0042 600/424 |
| 2014/0163356 | A2* | 6/2014 | Burnside | A61B 5/042 600/424 |
| 2014/0187942 | A1* | 7/2014 | Wang | A61B 8/0841 600/439 |
| 2015/0157296 | A1* | 6/2015 | Takagi | A61B 8/08 600/443 |
| 2015/0342561 | A1* | 12/2015 | Takeda | A61B 8/0841 600/424 |
| 2016/0000400 | A1* | 1/2016 | Korsten | A61B 8/0833 600/439 |

OTHER PUBLICATIONS

Korean Office Action issued in Korean Application No. 10-2012-0125597 dated Jan. 7, 2014.

* cited by examiner

ULTRASOUND SYSTEM AND METHOD FOR PROVIDING GUIDE LINE OF NEEDLE

RELATED APPLICATIONS

This application claims the benefit of Korean Patent Application No. 10-2012-0125597, filed on Nov. 7, 2012, in the Korean Intellectual Property Office, the disclosure of which is incorporated herein in its entirety by reference.

BACKGROUND

1. Field

One or more embodiments of the present invention relate to an ultrasound system, and more particularly, to an ultrasound system and method for providing a guide line corresponding to an introduction pathway, i.e., a pathway through which a needle is inserted.

2. Description of the Related Art

With the advancement in medical technologies, a technique for treating or examining a living body without direct incision is being used. The technique involves cutting a hole to a minimum size and inserting a medical needle such as an ablator or a biopsy needle into a living tissue having a lesion while observing images of the inside of the living body. This method is called "image-guided surgery" or "interventional surgical procedure" because it is performed by observing the inside of a living body using a medical imaging technique such as computerized tomography (CT) or magnetic resonance imaging (MRI). That is, the interventional surgical procedure is a technique for treatment or diagnosis whereby a medical needle is inserted directly through the skin into a lesion to be examined or treated while viewing images obtained from CT or MRI during surgery. The interventional surgical procedure usually does not require general anesthesia, involves reduced physical burden of a living body and little pain or torture, requires a short hospital stay, and has short recovery times after surgery. Thus, this procedure is less costly and more effective than a surgical treatment requiring incision.

However, when an interventional surgical procedure is performed by using CT or MR, it is difficult to obtain an image of a living body in real time. Furthermore, use of CT during surgery may pose a risk of long term radiation exposure to both a surgeon and a living body. On the other hand, use of an ultrasound system during an interventional surgical procedure may not only provide real-time ultrasound images but also pose little harm to a living body.

SUMMARY

One or more embodiments of the present invention include an ultrasound system and method for setting a guide line indicating a pathway through which a needle is inserted on an ultrasound image, based on a position and an angle at which the needle is introduced, which are detected by using the ultrasound image.

Additional aspects will be set forth in part in the description which follows and, in part, will be apparent from the description, or may be learned by practice of the presented embodiments.

According to one or more embodiments of the present invention, an ultrasound system includes an ultrasound data acquisition unit that transmits an ultrasound signal to a living body into which the needle is inserted, receives an ultrasound echo signal reflected from the living body, and acquires ultrasound data corresponding to each of a plurality of ultrasound images, and a processor that generates the plurality of ultrasound images by using the ultrasound data, creates a mask image for detecting a position and an angle at which the needle is introduced, detects the position and angle by using the mask image, and sets a guide line of the needle on the ultrasound image by using the position and angle.

The ultrasound system and method according to the embodiments of the present invention may provide a guide line corresponding to a pathway through which a needle is inserted (i.e., a direction in which the needle travels) without using additional devices such as a needle kit and a sensor.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
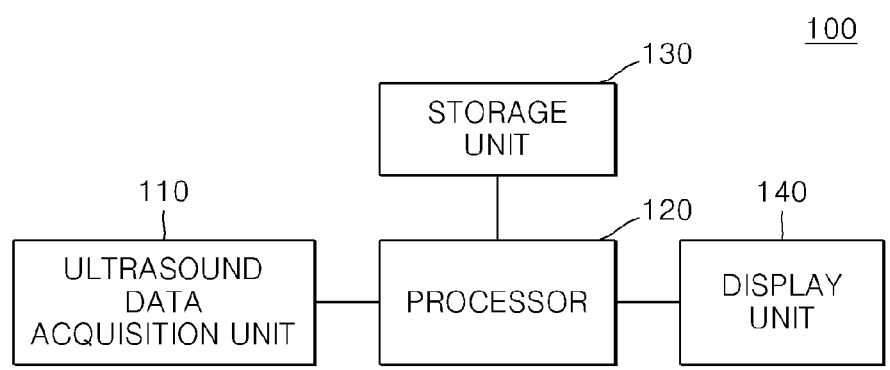
FIG. 1 is a block diagram showing a configuration of an ultrasound system according to an exemplary embodiment of the present invention.

Reference will now be made in detail to embodiments, examples of which are illustrated in the accompanying drawings, wherein like reference numerals refer to like elements throughout. As used herein, the term "and/or" includes any and all combinations of one or more of the associated listed items. Expressions such as "at least one of," when preceding a list of elements, modify the entire list of elements and do not modify the individual elements of the list.

FIG. 1 is a block diagram showing a configuration of an ultrasound system 100 according to an exemplary diagram of the present invention. Referring to FIG. 1, the ultrasound system 100 according to the present embodiment includes an ultrasound data acquisition unit 110, a processor 120, a storage unit 130, and a display unit 140. The ultrasound system 100 further includes a medical tool (not shown) that is inserted into a living body to remove a lesion within the living body. In the present embodiment, the medical tool may include a needle, but is not limited thereto.

The ultrasound data acquisition unit 110 is configured to transmit an ultrasound signal to a living body, receive an ultrasound echo signal reflected from the living body, and acquire ultrasound data corresponding to an ultrasound image. The living body includes an object such as a lesion, the heart, or the liver.

Figure 2:
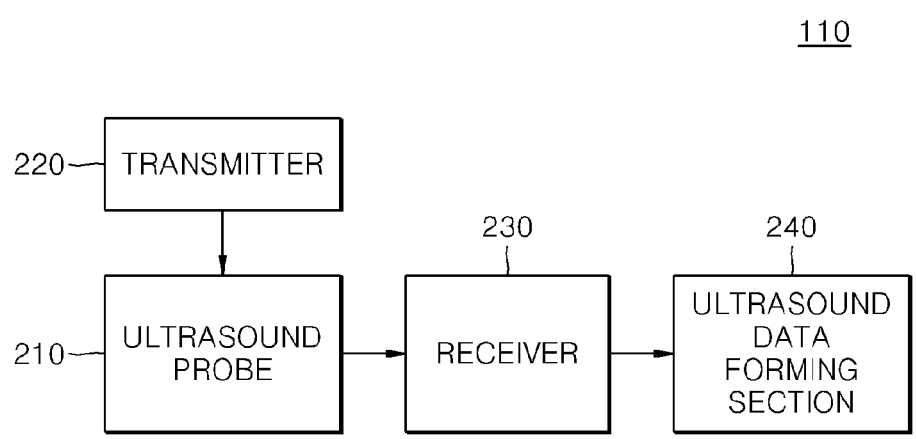
FIG. 2 is a block diagram showing a configuration of an ultrasound data acquisition unit in the ultrasound system of FIG. 1, according to an exemplary diagram of the present invention.

FIG. 2 is a block diagram showing a configuration of the ultrasound data acquisition unit 110 in the ultrasound system of FIG. 1, according to an exemplary diagram of the present invention. Referring to FIG. 2, the ultrasound data acquisition unit 110 includes an ultrasound probe 210, a transmitter 220, a receiver 230, and an ultrasound data forming section 240.

The ultrasound probe 210 includes a plurality of transducer elements (not shown) that convert electrical signals into ultrasound signals, and vice versa. The ultrasound probe 210 is configured to transmit an ultrasound signal to a living body and receive an ultrasound echo signal reflected from the living body to generate an electrical signal (hereinafter, referred to as a "reception signal"). The reception signal is an analog signal. The ultrasound probe 210 includes a linear probe, a convex probe, and a three-dimensional (3D) probe.

Figure 3:
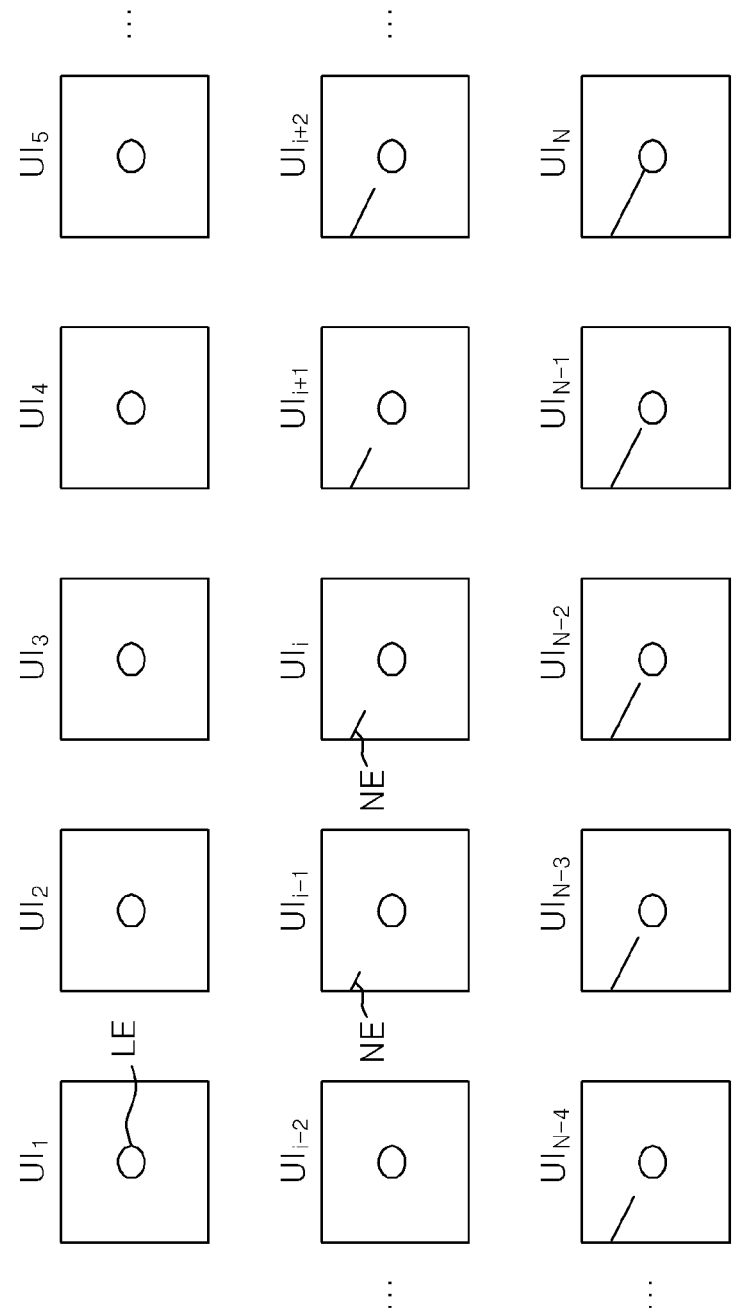
FIG. 3 is an exemplary diagram illustrating a plurality of ultrasound images.

The transmitter 220 controls the transmission of an ultrasound signal. The transmitter 220 also produces an electrical signal (hereinafter, referred to as a "transmission signal") that is used to obtain an ultrasound image in consideration of the transducer elements and a focal point. In the present embodiment, as shown in FIG. 3, the transmitter 220 sequentially creates a transmission signal that is used to obtain each of a plurality of ultrasound images $UI_N$ (N≥1). Thus, the ultrasound probe 210 converts the transmission signal sequentially received from the transmitter 220 into an ultrasound signal, transmits the ultrasound signal to a living body, and receives an ultrasound echo signal reflected from the living body to create a reception signal.

The receiver 230 performs analog-to-digital conversion on the reception signal provided by the ultrasound probe 210 to produce a digital signal. The receiver 230 also performs reception beamforming on the digital signal in consideration of the transducer elements and a focal point to create a focused reception signal. Since the reception beamforming may be performed by using various known methods, a detailed description thereof is omitted here. In the present embodiment, the receiver 230 performs analog-to-digital conversion on the reception signal sequentially received from the ultrasound probe 210 to produce a digital signal and performs reception beamforming on the digital signal in consideration of the transducer elements and a focal point to create a focused reception signal.

The ultrasound data forming section 240 creates ultrasound data corresponding to an ultrasound image by using the focused reception signal provided by the receiver 230. The ultrasound data includes radio frequency (RF) data. In the present embodiment, the ultrasound data forming section 240 generates ultrasound data corresponding to each of the plurality of ultrasound images $UI_N$ (N≥1) by using the focused reception signal sequentially received from the receiver 230. The ultrasound data forming section 240 may also perform various signal processings, such as gain control, needed to form ultrasound data, on the focused reception signal.

Referring back to FIG. 1, the processor 120 is connected to the ultrasound data acquisition unit 110. The processor 120 includes a central processing unit (CPU), a microprocessor, and a graphics processing unit (GPU).

Figure 4:
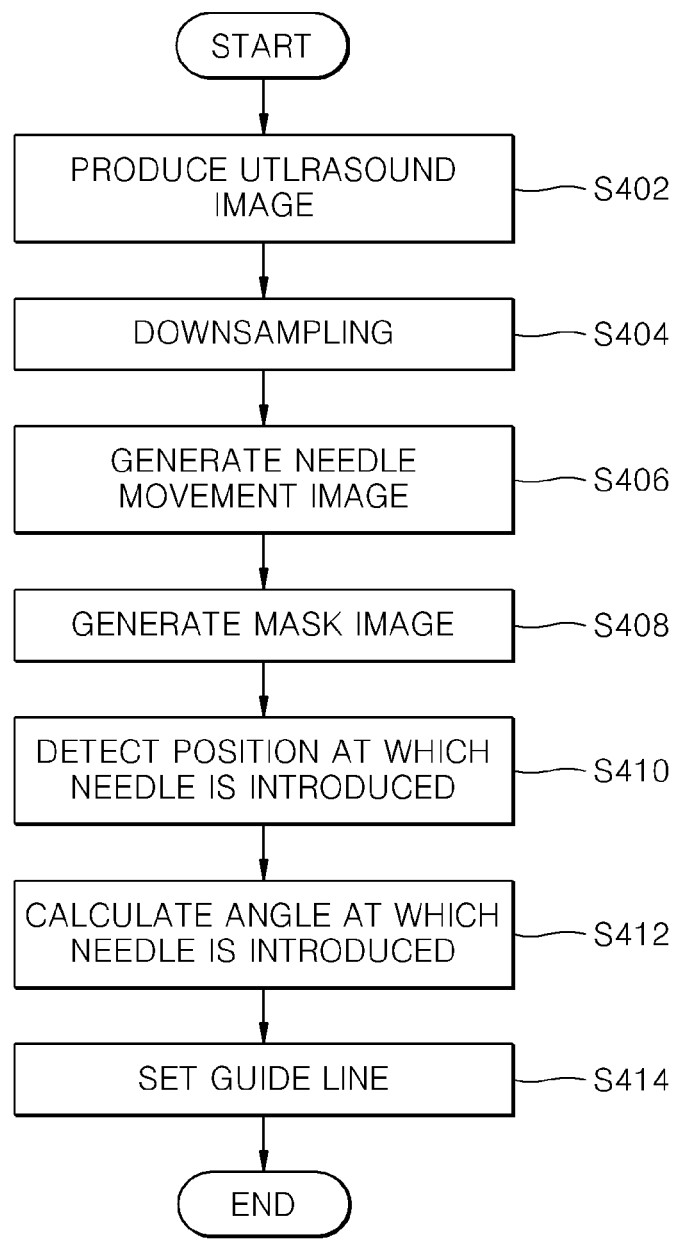
FIG. 4 is a flowchart of a process of setting a guide line of a needle according to an exemplary embodiment of the present invention.

FIG. 4 is a flowchart of a process of setting a guide line of a medical tool, i.e., a needle, according to an exemplary embodiment of the present invention. Referring to FIG. 4, the processor 120 produces an ultrasound image by using ultrasound data provided by the ultrasound data acquisition unit 110 (S402). In the present embodiment, the processor 120 creates a plurality of ultrasound images $UI_N$ (N≥1) by using ultrasound data sequentially received from the ultrasound data acquisition unit 110.

The processor 120 performs downsampling on the plurality of ultrasound images $UI_k$ (1≤k≤N) in order to reduce processing time and storage space thereof and creates a plurality of ultrasound images $CUI_k$ (1≤k≤N) (hereinafter called "copies of ultrasound images") (S404). Since the downsampling is performed by using various known methods, a detailed description thereof is omitted here.

The processor 120 generates a needle movement image by using a predetermined number of copies of ultrasound images among the plurality of copies of ultrasound images (S406). In the present embodiment, the processor 120 selects a predetermined number (e.g., five) of copies $CUI_{i-2}$, $CUI_{i-1}$, $CUI_{i+1}$, and $CUI_{i+2}$ of ultrasound images in a temporal direction with respect to an i-th copy $CUI_i$ of ultrasound image. The processor 120 generates a needle movement image by using the selected copies $CUI_{i-2}$, $CUI_{i-1}$, $CUI_i$, $CUI_{i+1}$, and $CUI_{i+2}$ of ultrasound images. For example, the processor 120 creates a needle movement image $NMI_i$ by using Equation (1) below:

$$NMI_i = \frac{|CUI_{i-2} - CUI_{i-1}| + |CUI_{i-1} - CUI_i| + |CUI_i - CUI_{i+1}| + |CUI_{i+1} - CUI_{i+2}|}{4} \quad (1)$$

The processor 120 creates a mask image by using an ultrasound image $UI_i$ and the needle movement image $NMI_i$ (S408). The mask image is an image for emphasizing a needle in the ultrasound image $UI_i$. In the present embodiment, the processor 120 may create a mask image $MI_i$ by using Equation (2) below:

$$MI_i = UI_i \times \alpha + NMI_i \times (1-\alpha) \quad (2)$$

where α is a weighting factor that is a preset value or a value set by a user.

Figure 5:
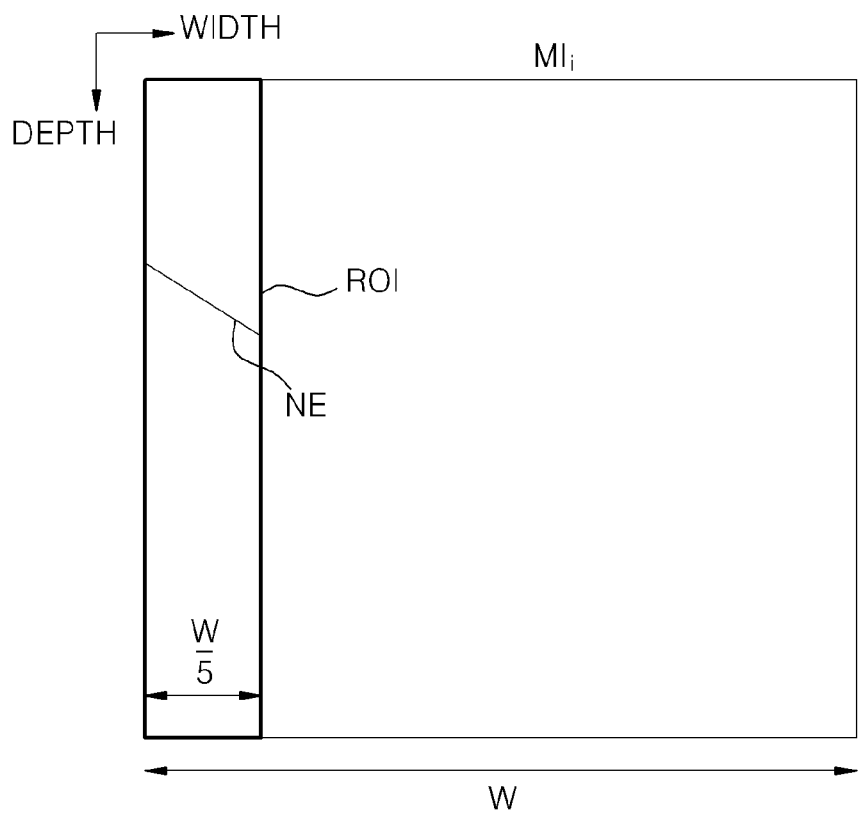
FIG. 5 is an exemplary diagram illustrating a mask image and a first region of interest (ROI) according to an exemplary embodiment of the present invention.
Figure 6:
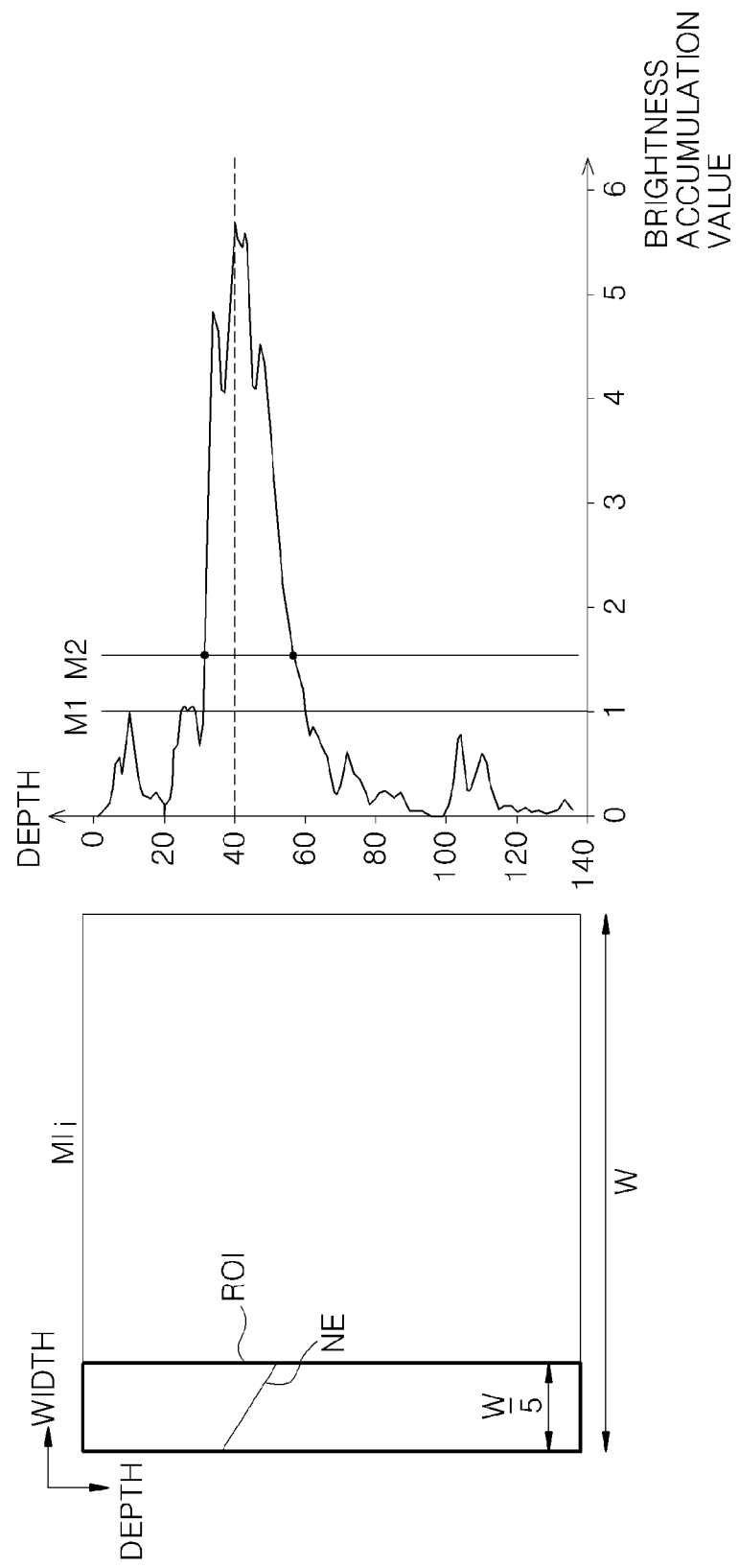
FIG. 6 is an exemplary diagram illustrating first cumulative brightness values and needle introduction positions with respect to a depth according to an exemplary embodiment of the present invention.

The processor 120 detects a position at which the needle is introduced (inserted) by using the mask image (S410). In the present embodiment, the processor 120 sets a region of interest (ROI) having a preset size on the mask image $MI_i$ in consideration of a direction in which the needle is introduced. In this case, the direction in which the needle is introduced may be manually set by the user, or automatically set by a system. For example, as shown in FIG. 5, the processor 120 sets an ROI having a size corresponding to one fifth of a width W of the mask image $MI_i$ from the leftmost side, in consideration of the direction in which the needle is introduced from the left side into the right side. As shown in FIG. 6, the processor 120 accumulates brightness values of pixels within the ROI for each depth of the mask image $MI_i$ along a width direction of the mask image $MI_i$ and calculates first cumulative brightness (intensity) values. The processor 120 detects a maximum cumulative brightness value among the calculated first cumulative brightness values and a depth corresponding to the maximum cumulative brightness value as a position NIP at which the needle is introduced.

Figure 7:
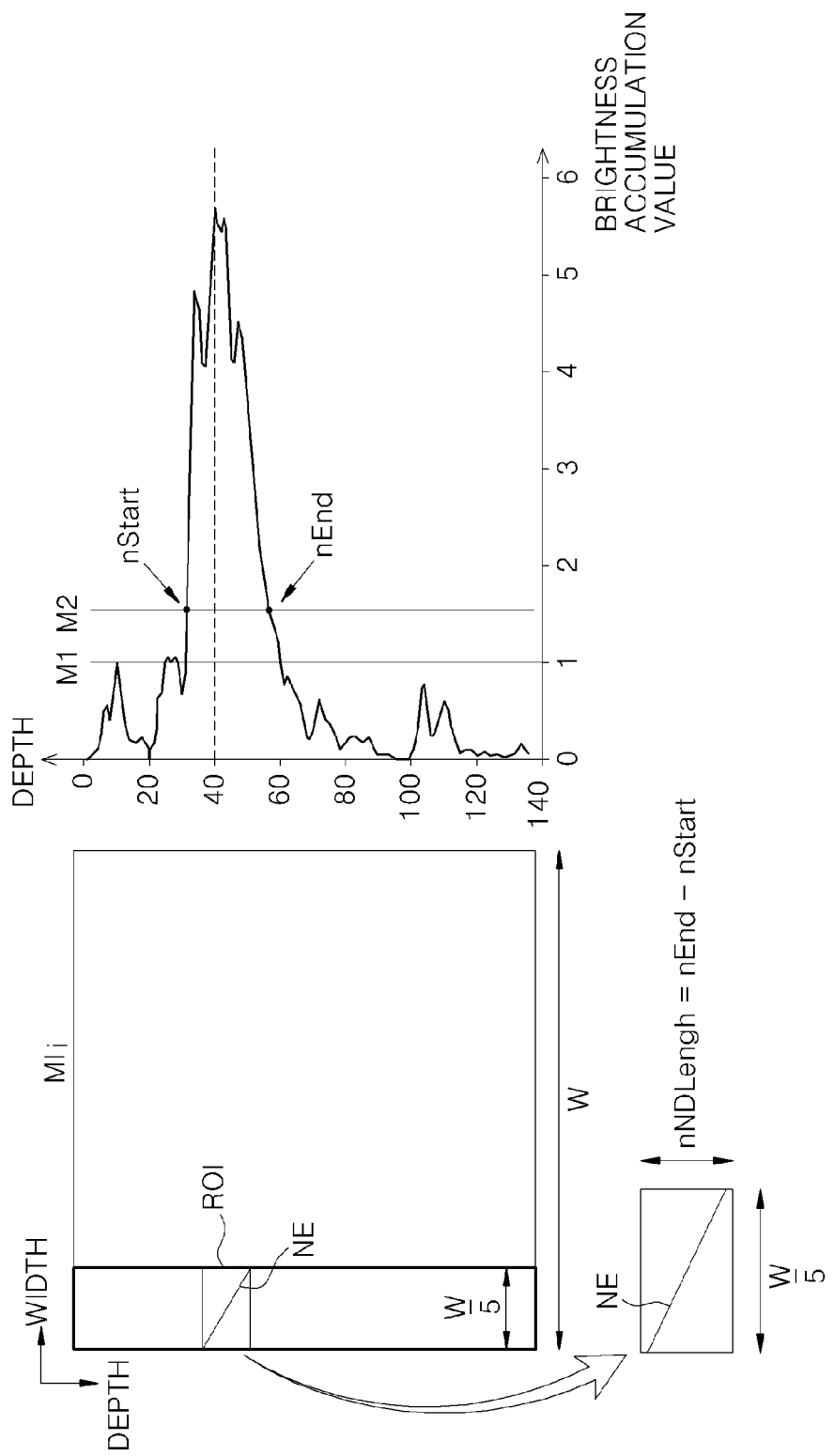
FIG. 7 is an exemplary diagram illustrating a first mean value, a second mean value, a start point, an end position, and a length between the start point and the end point that are needed for calculating an angle at which a needle is introduced according to an exemplary embodiment of the present invention.

The processor 120 calculates an angle at which the needle is introduced (inserted) based on the position NIP at which the needle is introduced (S412). In one embodiment, as shown in FIG. 7, the processor 120 calculates a first mean value M1 of the first cumulative brightness values and a second mean value M2 of second cumulative brightness values obtained by subtracting the first mean value M1 from each of the first cumulative brightness values. The processor 120 then detects intersection points of the second mean value M2 and the first cumulative brightness values as a start point nStart and an end point nEnd. The processor 120 calculates an angle at which the needle is introduced based on a length nNDLength from the start point nStart to the end point nEnd. For example, the processor 120 may calculate an angle θ at which the needle is introduced by using Equation (3) below:

$$\theta = \tan^{-1}\left(\frac{nNDLength}{\frac{W}{5}}\right) \quad (3)$$

Figure 8:
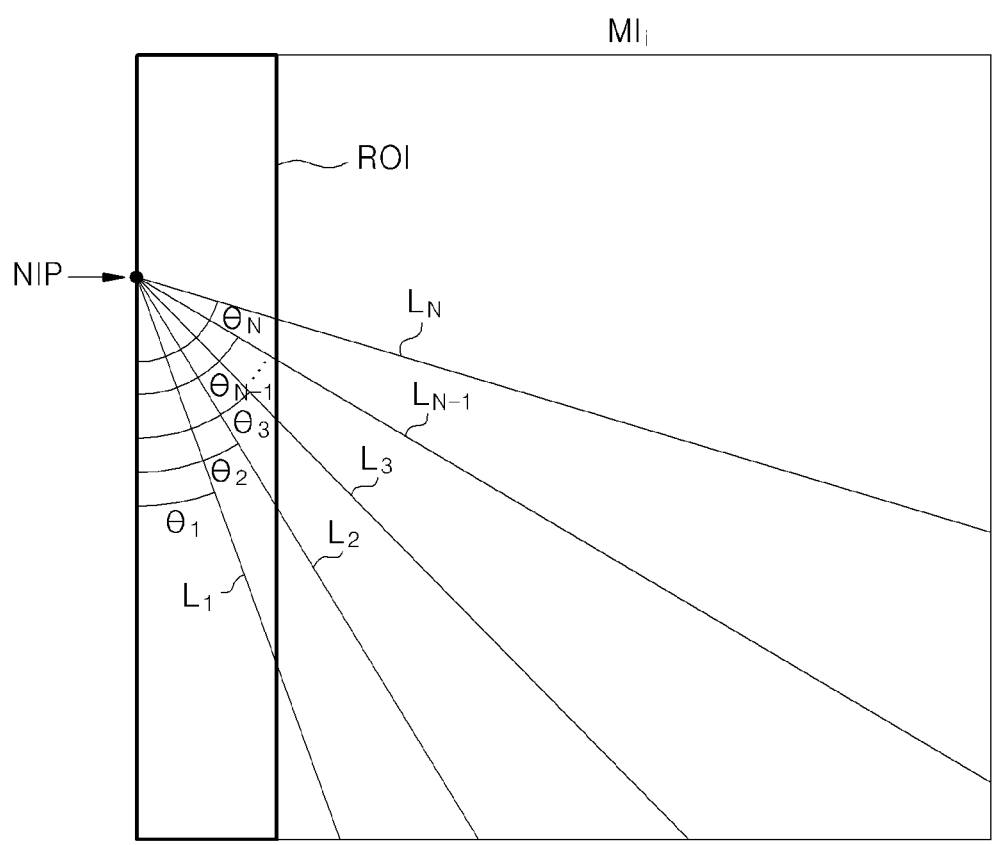
FIG. 8 is an exemplary diagram illustrating a second region of interest (ROI) and a plurality of angles and lines for calculating an angle at which a needle is introduced according to an exemplary embodiment of the present invention.

In another embodiment, as shown in FIG. 8, the processor 120 sets a plurality of angles $\theta_i$ (1≤i≤N) based on the position NIP at which the needle is introduced, and sets a plurality of lines $L_i$ (1≤i≤N) corresponding to the plurality of angles $\theta_i$ from the position NIP, respectively, on a mask image $MI_i$. The processor 120 then calculates third cumulative brightness values of pixels corresponding to the plurality of lines $L_i$ (1≤i≤N). The processor 120 detects a maximum cumulative brightness value among the third calculated cumulative brightness values and an angle corresponding to the maximum cumulative brightness value as an angle at which the needle is introduced.

Figure 9:
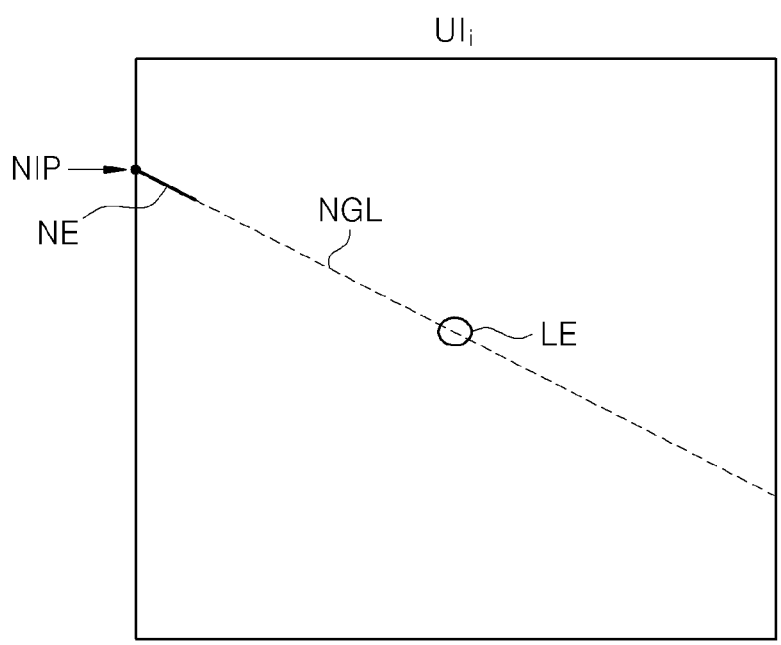
FIG. 9 is an exemplary diagram illustrating a guide line of a needle according to an exemplary embodiment of the present invention.

Next, as shown in FIG. 9, the processor 120 sets a needle guide line LGL on the ultrasound image $UI_i$ based on the detected position and angle at which the needle is introduced (S414).

While the ultrasound image is downsampled and a needle movement image is created by using the downsampled image, the needle movement image may be produced by using the ultrasound image without performing the downsampling.

Referring back to FIG. 1, the storage unit 130 stores ultrasound data acquired by the ultrasound data acquisition unit 110 as well as ultrasound images (original ultrasound images and copies of ultrasound images) generated by the processor 120. The storage unit 130 also stores a position and an angle at which a needle is introduced, which are detected by the processor 120.

The display unit 140 displays ultrasound images (original ultrasound images and/or copies of ultrasound images) generated by the processor 120, as well as a needle guide line set on an ultrasound image.

While one or more embodiments of the present invention have been described with reference to the figures, it will be understood by those of ordinary skill in the art that various changes in form and details may be made therein without departing from the spirit and scope of the present invention as defined by the following claims.

What is claimed is:

1. An ultrasound system comprising:
an ultrasound probe configured to transmit an ultrasound signal to a living body into which a needle is inserted, and receive an ultrasound echo signal reflected from the living body;
a processor configured to:
generate a plurality of ultrasound images by using the ultrasound data,
perform downsampling on each of the plurality of ultrasound images to create a plurality of copies of ultrasound images in order to reduce processing time and storage space,
create a needle movement image by using a predetermined number of copies of ultrasound images among the plurality of copies of ultrasound images,
create a mask image for detecting a position and an angle at which the needle is introduced by using a first ultrasound image of the plurality of ultrasound images and the needle movement image,
set a region of interest (ROI) having a preset size on the mask image in consideration of a direction in which the needle is introduced,
within the ROI, add brightness values of pixels, having a same depth from a minimum depth to a maximum depth of the ROI, along a width direction of the mask image, to thereby calculate first cumulative brightness values corresponding to respective depths,
detect a maximum cumulative brightness value among the calculated first cumulative brightness values,
detect a depth corresponding to the maximum cumulative brightness value as a position at which the needle is introduced in the mask image,
calculate an angle at which the needle is introduced in the mask image based on the position at which the needle is introduced in the mask image, and
set a guide line which is a route for the needle to be inserted on the first ultrasound image by using the position and angle at which the needle is introduced in the mask image; and
a display configured to display the guide line and the position at which the needle is introduced, overlaid on the first ultrasound image.

2. The ultrasound system of claim 1, wherein the processor is further configured to select the predetermined number of copies of ultrasound images in a temporal direction with respect to each of the plurality of copies of ultrasound images and generates the needle movement image by using the selected copies of ultrasound images.

3. The ultrasound system of claim 2, wherein the processor is further configured to generate the needle movement image by using $$NMI_i = \frac{|CUI_{i-2} - CUI_{i-1}| + |CUI_{i-1} - CUI_i| + |CUI_i - CUI_{i+1}| + |CUI_{i+1} - CUI_{i+2}|}{4}$$

where $NMI_i$ is the needle movement image, and $CUI_{i-2}$ through $CUI_{i+2}$ are the selected copies of ultrasound images.

4. The ultrasound system of claim 1, wherein the mask image is for emphasizing the needle in the first ultrasound image.

5. The ultrasound system of claim 1, wherein the processor is further configured to create the mask image by using $$MI = UI \times \alpha + NMI \times (1-\alpha)$$

where MI is the mask image, UI is the first ultrasound image, α is a weighting factor, and NMI is the needle movement image.

6. The ultrasound system of claim 1, wherein the processor is further configured to calculate a first mean value of the first cumulative brightness values and a second mean value of second cumulative brightness values that are obtained by subtracting the first mean value from each of the first cumulative brightness values, detect a start point and an end point based on the first cumulative brightness values and the second mean value, calculate a length between the start point and the end point, and calculate the angle at which the needle is introduced based on the length.

7. The ultrasound system of claim 6, wherein the processor is further configured to calculate the angle at which the needle is introduced by using $$\theta = \tan^{-1}\left(\frac{nNDLength}{\frac{W}{5}}\right)$$

where θ is the angle at which the needle is introduced, nNDLength is the length, and W is a width of the mask image.

8. The ultrasound system of claim 1, wherein the processor is further configured to set a plurality of angles based on the position at which the needle is introduced, set a plurality of lines corresponding to the plurality of angles $\theta_i$ from the position, respectively, on the mask image, calculate third cumulative brightness values of pixels in the plurality of lines, detect a maximum cumulative brightness value among the third cumulative brightness values, and detect an angle corresponding to the maximum cumulative brightness value as the angle at which the needle is introduced.

9. A method of providing a guide line of a needle using an ultrasound system, the method comprising:
   transmitting an ultrasound signal to a living body into which the needle is inserted, receiving an ultrasound echo signal reflected from the living body, and acquiring ultrasound data corresponding to each of a plurality of ultrasound images;
   generating the plurality of ultrasound images by using the ultrasound data;
   performing downsampling on each of the plurality of ultrasound images to create a plurality of copies of ultrasound images in order to reduce processing time and storage space;
   creating a needle movement image by using a predetermined number of copies of ultrasound images among the plurality of copies of ultrasound images;
   creating a mask image for detecting a position and an angle at which the needle is introduced by using a first ultrasound image of the plurality of ultrasound images and the needle movement image;
   setting a region of interest (ROI) having a preset size on the mask image in consideration of a direction in which the needle is introduced;
   within the ROI, adding brightness values of pixels, having a same depth from a minimum depth to a maximum depth of the ROI, along a width direction of the mask image, to thereby calculate first cumulative brightness values corresponding to respective depths;
   detecting a maximum cumulative brightness value among the calculated first cumulative brightness values;
   detecting a depth corresponding to the maximum cumulative brightness value as a position at which the needle is introduced in the mask image;
   calculating an angle at which the needle is introduced in the mask image based on the position at which the needle is introduced in the mask image;
   setting a guide line of the needle on the first ultrasound image by using the position and angle at which the needle is introduced in the mask image; and
   displaying the guide line and the position at which the needle is introduced, overlaid on the first ultrasound image.

10. The method of claim 9, wherein the creating of the mask image comprises selecting the predetermined number of copies of ultrasound images in a temporal direction with respect to each of the plurality of copies of ultrasound images and generating the needle movement image by using the selected copies of ultrasound images.

11. The method of claim 10, wherein in the generating of the needle movement image, the needle movement image is generated by using $$NMI_i = \frac{|CUI_{i-2} - CUI_{i-1}| + |CUI_{i-1} - CUI_i| + |CUI_i - CUI_{i+1}| + |CUI_{i+1} - CUI_{i+2}|}{4}$$

where $NMI_i$ is the needle movement image, and $CUI_{i-2}$ through $CUI_{i+2}$ are the selected copies of ultrasound images.

12. The method of claim 9, wherein the creating of the mask image comprises creating the mask image for emphasizing the needle in the ultrasound image by using the first ultrasound image and the needle movement image.

13. The method of claim 12, wherein in the creating of the mask image, the mask image is created by using $$MI = UI \times \alpha + NMI \times (1-\alpha)$$

where MI is the mask image, UI is the first ultrasound image, and α is a weighting factor.

14. The method of claim 9, wherein the calculating of the angle at which the needle is introduced comprises:
   calculating a first mean value of the first cumulative brightness values;
   calculating a second mean value of second cumulative brightness values that are obtained by subtracting the first mean value from each of the first cumulative brightness values;
   detecting a start point and an end point based on the first cumulative brightness values and the second mean value;
   calculating a length between the start point and the end point; and
   calculating the angle at which the needle is introduced based on the length.

15. The method of claim 14, wherein in the calculating of the angle at which the needle is introduced, the angle is calculated by using $$\theta = \tan^{-1}\left(\frac{nNDLength}{\frac{W}{5}}\right)$$

where θ is the angle at which the needle is introduced, nNDLength is the length, and W is a width of the mask image.

16. The method of claim 9, wherein the calculating of the angle at which the needle is introduced comprises:
- setting a plurality of angles based on the position at which the needle is introduced;
- setting a plurality of lines corresponding to the plurality of angles $\theta_i$ from the position, respectively, on the mask image;
- calculating third cumulative brightness values of pixels in the plurality of lines;
- detecting a maximum cumulative brightness value among the third cumulative brightness values; and
- detecting an angle corresponding to the maximum cumulative brightness value as the angle at which the needle is introduced.

* * * * *